(12) United States Patent
Brandestini et al.

(10) Patent No.: US 9,091,663 B2
(45) Date of Patent: Jul. 28, 2015

(54) DEVICE FOR DETERMINING THE WEAR OF A CARBON CERAMIC BRAKE DISK

(75) Inventors: Marco Brandestini, Lachen (CH); Peter Stierli, Uerikon (CH)

(73) Assignee: PROCEQ SA, Schwerzenbach (CH)

( * ) Notice: Subject to any disclaimer, the term of this patent is extended or adjusted under 35 U.S.C. 154(b) by 331 days.

(21) Appl. No.: 13/546,640

(22) Filed: Jul. 11, 2012

(65) Prior Publication Data
US 2013/0015849 A1 Jan. 17, 2013

(30) Foreign Application Priority Data
Jul. 12, 2011 (DE) ...................... 20 2011 103 105 U

(51) Int. Cl.
*G01N 27/90* (2006.01)
*G01N 27/80* (2006.01)

(52) U.S. Cl.
CPC ............ *G01N 27/9033* (2013.01); *G01N 27/80* (2013.01)

(58) Field of Classification Search
CPC ......... G01R 33/02; G01R 33/12; G01N 27/82
USPC ........................... 324/234–240, 241, 249, 225
See application file for complete search history.

(56) References Cited

U.S. PATENT DOCUMENTS

| | | | | |
|---|---|---|---|---|
| 501,977 A * | 7/1893 | Gulliver et al. ............ 400/297.1 |
| 2,150,922 A * | 3/1939 | Hay ................................ 324/232 |
| 4,922,201 A | 5/1990 | Vernon et al. |
| 5,028,100 A | 7/1991 | Valleau et al. |
| 5,296,807 A * | 3/1994 | Kousek et al. ................. 324/235 |
| 5,510,709 A * | 4/1996 | Hurley et al. .................. 324/242 |
| 6,037,768 A | 3/2000 | Moulder et al. |
| 6,966,816 B2 * | 11/2005 | Swedek et al. ..................... 451/5 |
| 7,238,308 B2 | 7/2007 | Rosenloecher |
| 7,309,609 B2 * | 12/2007 | Christ et al. ................... 436/149 |
| 7,560,920 B1 * | 7/2009 | Ouyang et al. ................. 324/242 |
| 7,993,549 B2 | 8/2011 | Niewohner et al. |
| 2002/0144866 A1 | 10/2002 | Martin |
| 2004/0124087 A1 | 7/2004 | Christ et al. |
| 2004/0126535 A1 | 7/2004 | Sommer et al. |
| 2006/0158181 A1 | 7/2006 | Shoji |
| 2006/0170420 A1 * | 8/2006 | Nishimizu et al. ............ 324/239 |
| 2007/0108971 A1 | 5/2007 | Dardik et al. |

FOREIGN PATENT DOCUMENTS

| | | |
|---|---|---|
| DE | 10 2008 051 802 A1 | 4/2010 |
| EP | 1 387 166 A2 | 2/2004 |
| EP | 2 182 347 A2 | 5/2010 |

OTHER PUBLICATIONS

"Eddy Current Testing for Safe Components", pp. 1-31, Apr. 30, 2011.
Search report from E.P.O. in related application No. 12004765 9, mail date is Oct. 4, 2012.

(Continued)

*Primary Examiner* — Patrick Assouad
*Assistant Examiner* — Taqi Nasir
(74) *Attorney, Agent, or Firm* — Greenblum & Bernstein, P.L.C.

(57) ABSTRACT

Device for determining wear in a carbon ceramic brake disk. The device includes a coil arrangement having at least one coil structured and arranged to generate a magnetic field in the brake disk and to detect an eddy current in the brake disk, and an arcuate measuring area.

17 Claims, 4 Drawing Sheets

(56) References Cited

OTHER PUBLICATIONS

P. Plotard et al., "Non Destructive Inspection for Carbon—Carbon with Adapted Coating for Oxidation", Aerospatiale Aquitaine, pp. 1-9 (date unknown).

Thomas D. Nixon et al., "Non-Destructive Characterization of SiC Coated Carbon—Carbon Composites by Multiple Techniques", 24th International Sampe Technical Conference, vol. 24, Oct. 20-22, 1992, pp. T12-T27.

* cited by examiner

DEVICE FOR DETERMINING THE WEAR OF A CARBON CERAMIC BRAKE DISK

CROSS REFERENCE TO RELATED APPLICATIONS

This application claims the priority under 35 U.S.C. §119 (a) of German Utility Model Application 20 2011 103 105.9 filed Jul. 12, 2011, the disclosure of which is expressly incorporated by reference herein in its entirety.

BACKGROUND OF THE INVENTION

1. Field of the Invention

Embodiments of the invention relates to a device for determining the wear of a carbon ceramic brake disk. The device includes at least one coil for generating a magnetic field in the brake disk and for detecting an eddy current in the brake disk.

2. Discussion of Background Information

A "carbon ceramic brake disk" is a brake disk comprising a carbon ceramic, wherein the carbon ceramic comprises a ceramic matrix as well as carbon fibers embedded in the matrix.

In such carbon ceramic brake disks an oxidation of the carbon fibers and therefore wear occurs due to high operating temperatures. This wear cannot be reliably recognized by mere optical inspection. An improved recognition of wear is achieved by inductive methods of measurement. The principle used in this type of measurements is based on eddy current damping; either using two coils (EP 1 387 166) operating continuously, or one or two coils in pulsed operation (DE 10 2008 051 802). The disclosures of EP 1 387 166 and DE 10 2008 051 802 are expressly incorporated by reference herein in their entireties. In these documents the excellent correlation between the inductive measurement and a gravimetric determination of the wear is disclosed. A conventionally traded profometer (www.proceq.com) is used as measuring device. Using these types of techniques, it is not necessary to disassemble the brake disk for measurement. It is also noted that the measuring values are independent on soiling and the presence of liquids.

The by far largest problem of such procedures lies in the fact that, due to the unavoidable inhomogeneity of the material, the measured values can differ strongly as a function of location (variations up to 100% are observed). A further variation is caused by the venting ducts extending within the disk. A conventional device can, upon a dislocation of a few millimeters, display a value that deviates by more than 10%. Since the drop of the measured value between a new and a worn disk is at approximately 40 to 50%, such a location dependence is greatly disadvantageous for a measurement.

DE 10 2008 051 802 describes a positioning technique by a gauge and mechanical positioning device, which, however, is found to non-viable.

Further it must be noted that reliable measuring values can only be recorded when the measuring device lies exactly against the disk, which leads to additional requirements regarding the shape of the device if the same is to be operated by hand at a location of service.

A further disturbing factor is due to the metallic elements, such as the caliper, axle shaft and fender, present around a built-in brake disk.

SUMMARY OF THE EMBODIMENTS

Therefore, embodiments of the invention are directed to a device of the type mentioned above that allows a more reliable measurement of the wear.

According to embodiments, the device for determining wear in a carbon ceramic brake disk includes a coil arrangement having at least one coil adapted and structured to generate a magnetic field in the brake disk and for detecting an eddy current in the brake disk. The coil arrangement has an arcuate measuring area.

In this context, the "measuring area" is the area in a measuring plane (i.e., in a plane parallel to the plane of the coils) that is reached by the field of the coil or coils during the measurement. In particular, the measuring area includes those locations in the measuring plane where the flux of the magnetic field generated by the coil(s) is at least 50% of a maximum value of the flux of the magnetic field in the measuring plane.

By the measuring area in accordance with the embodiments, a non-local measurement can be carried out over an extended region of the brake disk, which makes the measurement less sensitive to local inhomogeneities of the carbon ceramic.

Advantageously, the coil arrangement comprises at least three coils, in particular more than three coils, as well as a drive for generating, by means of the coils, a magnetic field in the measuring area.

Embodiments of the invention are directed to a device for determining wear in a carbon ceramic brake disk. The device includes a coil arrangement having at least one coil structured and arranged to generate a magnetic field in the brake disk and to detect an eddy current in the brake disk, and an arcuate measuring area.

According to embodiments, the arcuate measuring area may be positionable in a ring having a radial width smaller than 2 cm and an inner radius between 10 and 15 cm, and a length tangentially along the ring of at least 8 cm.

In accordance with other embodiments of the invention, the at least one coil can include at least three coils structured and arranged to generate a magnetic field in the measuring area.

Further, the at least one coil may include more than three coils structured and arranged to generate a magnetic field in the measuring area. The device can also include a common carrier plate on which the coils. The coils can be formed by conductive leads on the carrier plate. Moreover, each coil can extend around a center and the centers of the coils may be arranged on an arcuate curve. The centers of the coils can be arranged on a segment of a circle. Still further, each coil may extend around a center and the centers of the coils may be arranged on at least two arcuate, parallel curves. The centers of the coils can be arranged on at least two segments of concentric circles. The device may also include a common carrier plate on which the coils are arranged, and the common carrier plate one of forming a measuring surface or abutting on an inner side of a wall section forming the measuring surface. Further, each two neighboring coils on different curves can be poled anti-parallel to each other.

According to still other embodiments of the instant invention, the device may further include a voltage supply and a driver. The driver can be structured and arranged to connect the coils, in parallel to each other, to the voltage supply. The driver can be structured and arranged to disconnect the coils from the voltage supply and to sum inductive voltages generated over the coils after disconnecting the coils from the voltage supply.

In accordance with further embodiments of the invention, mutually neighboring coils can be poled anti-parallel to each other.

According to still other embodiments, the device may also include a housing and stops arranged on the housing being structured and arranged to radially abut against the brake disk.

The device can also include a measuring surface structured and arranged to abut against a front side of the brake disk. The stops can include projections extending transversally to the measuring surface. The projections may include rollers. The device can also include a light source for generating a light field as a positioning aid. The light source and the stops can be mutually arranged to generate a light strip on a front face of the brake disk upon abutting the device against the brake disk.

According to still other embodiments, the device can also include a light source structured and arranged to generate a light field as a positioning aid.

In accordance with still yet other embodiments of the present invention, a diameter of the at least one coil can be between 10 and 15 mm.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
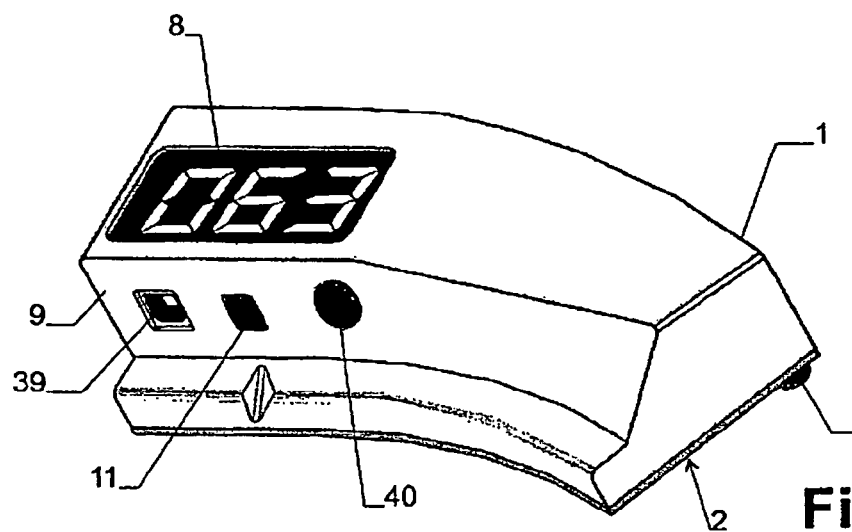
FIG. 1 shows a first perspective view of the device.
Figure 2:
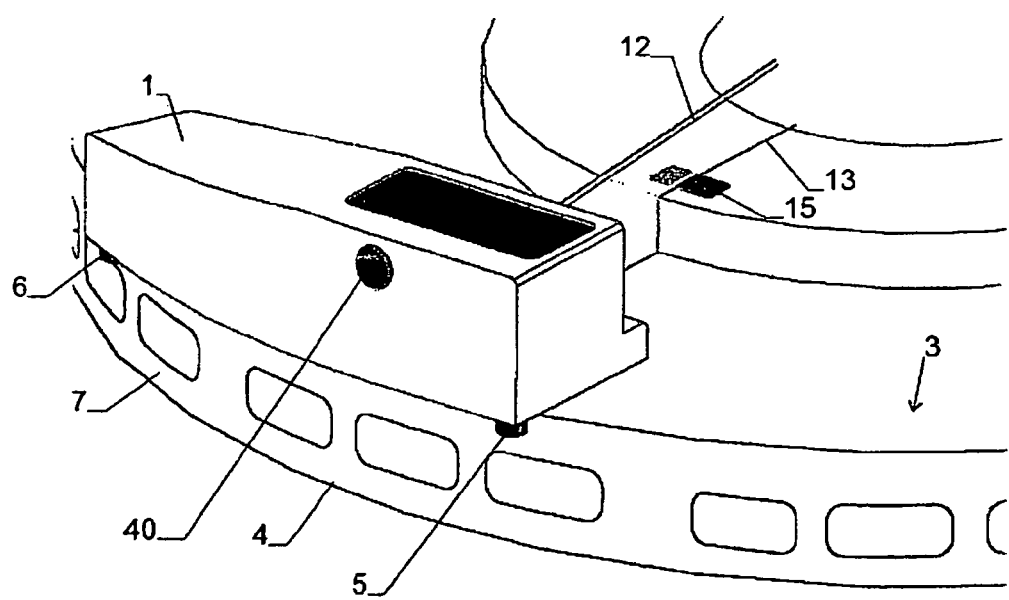
FIG. 2 shows a view of the device abutting against a brake disk.

The device illustrated in FIGS. 1 and 2 include a housing 1 with a measuring surface 2 intended to abut against a front face 3 of brake disk 4 during the measurement. Further, stops 5, 6 are provided on housing 1 to extend transversally, in particular, perpendicularly, to measuring surface 2. Stops 5, 6 are arranged to radially abut housing 1 against an outer edge 7 of brake disk 4, i.e., they are used to radially align housing 1 with respect to brake disk 4. Stops 5, 6 are designed as projections that extend over measuring surface 2. Advantageously, exactly two such projections are employed in order to ensure a defined radial abutment on brake disk 4.

The device further includes a display 8, advantageously arranged on a side of housing 1 that is opposite to measuring surface 2 so that it can be seen by the user. When the device is abutting correctly against brake disk 4, a side 9 of housing 1 is arranged to face the axle of brake disk 4. Further, side 9 includes a light source 11, which can include, e.g., a semiconductor laser having a light beam is extended in a direction perpendicular to front face 3 to form a planar light field 12. Planar light field 12 can serve as a positioning help because light source 11 and stops 5, 6 should preferably be mutually aligned so that, when the device correctly abuts against brake disk 4, a strip of light 13 is created on front face 3. The user can use strip of light 13 for azimuthally aligning the device in a defined manner with respect to one or more marks 14 arranged on brake disk 4. This solution requires no additional mechanical marker and is suited for all disk sizes. For better identification, light source 11 may be modulated in brightness.

The user can place housing 1 against brake disk 4 in the manner shown in FIG. 2, where the projections 5, 6 align the device radially and measuring surface 2 provides an axial alignment. To move the device to the correct azimuthal angle position, the user moves it along the circumference of brake disk 4. To simplify this motion, projections 5, 6 can be formed by rollers, e.g., rotatable cylinders, which roll along outer edge 7 of brake disk 4.

Figure 3:
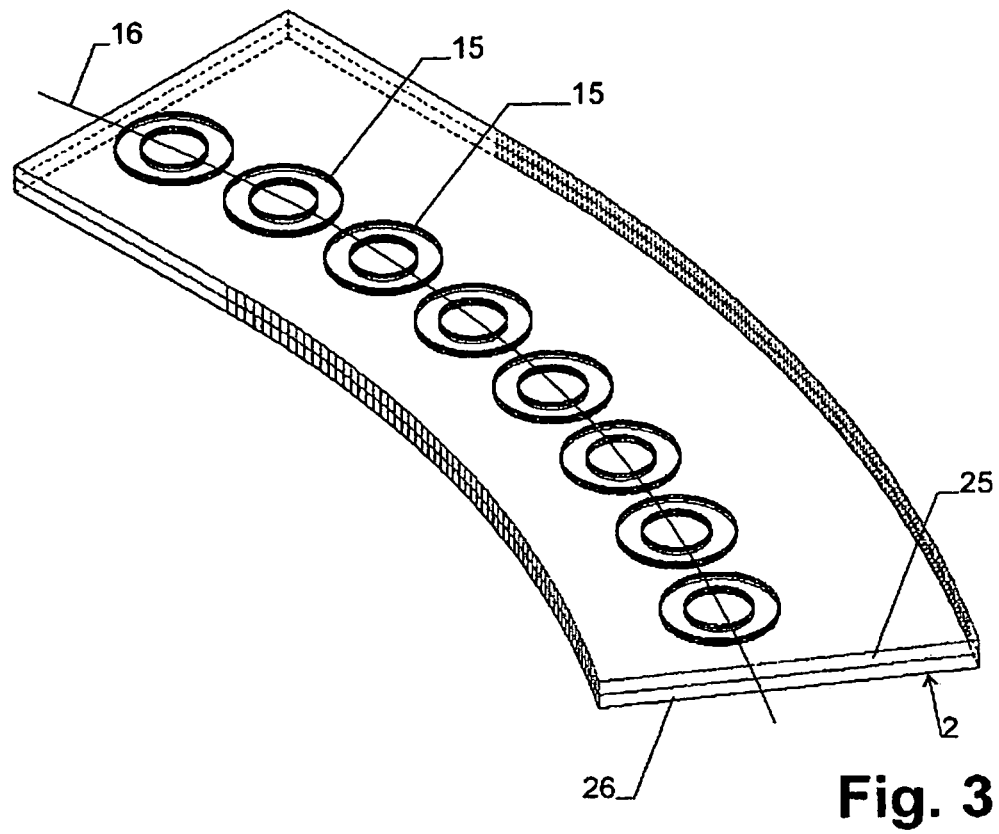
FIG. 3 shows a representation of the arrangement of the measuring coils.

As has been mentioned, the measurement is carried out by one or more coils. FIG. 3 shows an advantageous coil arrangement with several coils 15. In this embodiment, coils 15 are arranged side by side in a row, such that their centers lie along an arcuate curve 16, in particular a segment of a circle. The center of a circular coil is understood to be the axis that the coil is wound around.

Figure 4:
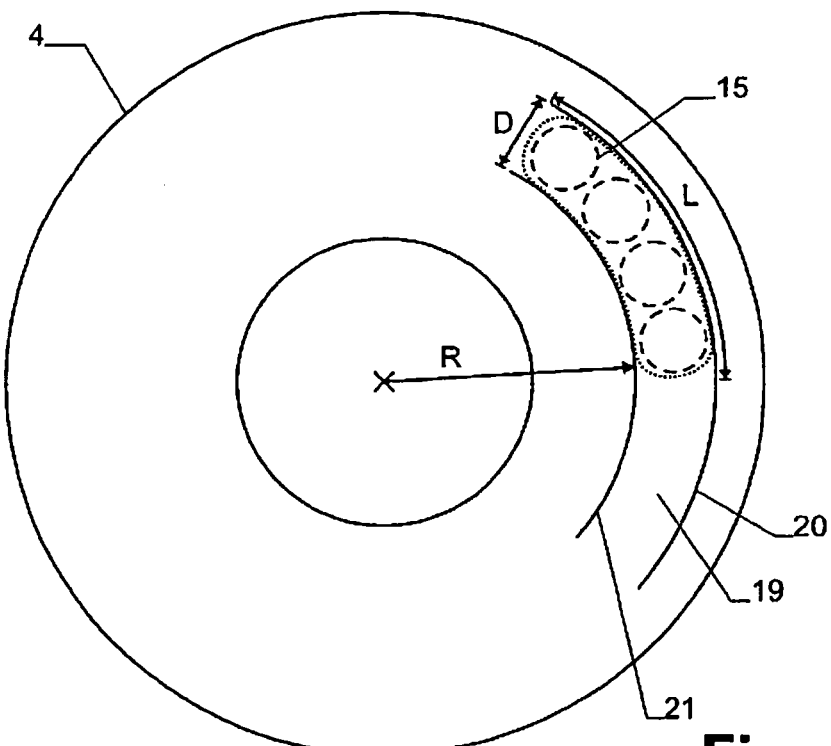
FIG. 4 is a schematic representation of the measuring area on the brake disk.

Coils 15 form an arcuate measuring area 18, as it is shown in dashed lines in FIG. 4. Measuring area 18 lies within a ring 19 between two concentric circle lines 20, 21. Radial width D of the ring (i.e., the distance between circle lines 20, 21) is smaller than 2 cm. Length L of measuring area 18 measured tangentially along the ring is at least 8 cm. Inner radius R of ring 19 lies between 10 and 15 cm. With a measuring area 18 of this type, a substantial region of a conventional brake disk can be reached, without metallic parts of the attachment or edge regions of the brake disk falling within measuring area 18.

Figure 7:
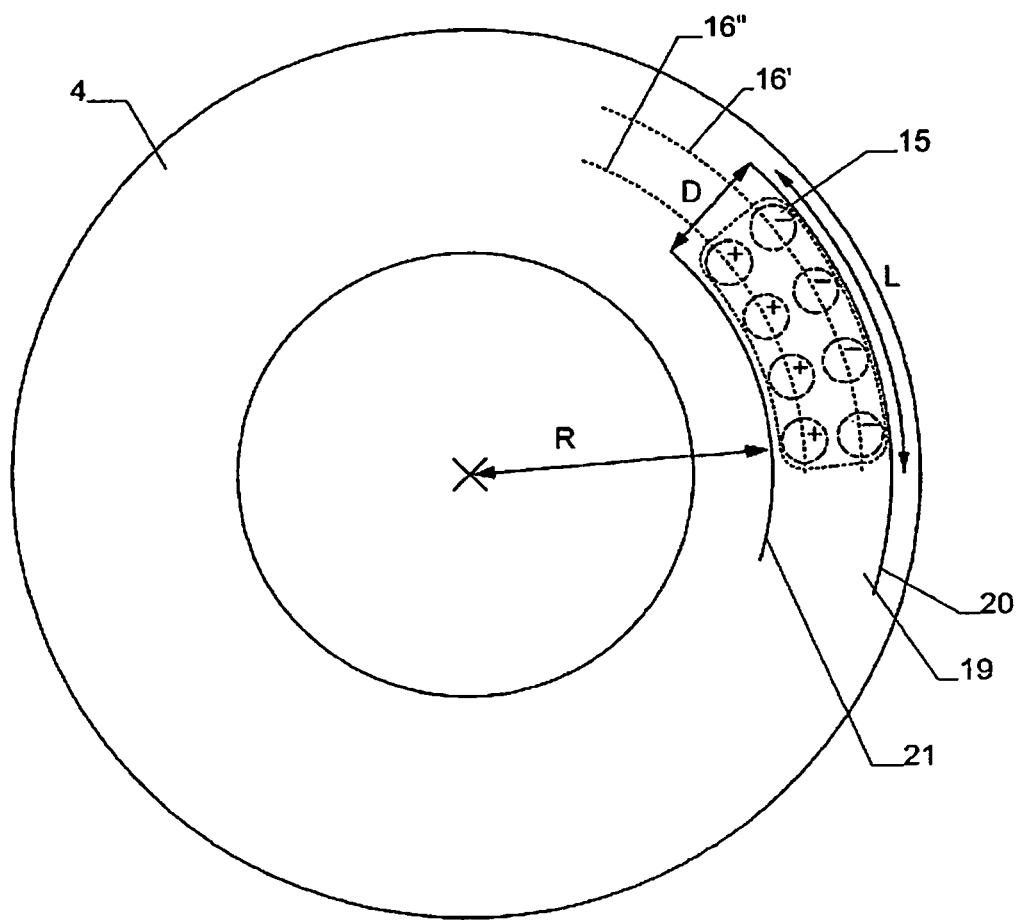
FIG. 7 shows a device with two rows of measuring coils.

Instead of a single row of coils 15, it is also possible to use at least two rows of coils 15. This is illustrated in FIG. 7, where the two rows of coils 15 are arranged on two parallel, arcuate curves 16', 16", in particular, on two segments of concentric circles. Advantageously, each two neighboring coils 15 arranged on different curves are poled anti-parallel, as it is shown by the signs + and − in FIG. 7. In this manner, the field of one coil is deflected into the respective neighboring coil, so that it extends through a substantial volume of brake disk 4 without extending very deeply into brake disk 4. This allows preventing the field from exiting through the opposite side of brake disk 4, where it might be affected by metal parts.

In principle, also in the embodiment of FIGS. 3 and 4, each two neighboring coils can be poled anti-parallel. However, it has also been found that the use of anti-parallel poled coils in an arrangement with two rows of coils according to FIG. 7 is particularly advantageous.

The term "poled anti-parallel" as used in the embodiments is to be understood to mean that the fields generated by the two coils are anti-parallel to each other. This can be achieved, e.g., by winding the two coils in opposite winding directions and by sending currents of equal phases through them, or by winding the two coils in the same winding direction and by sending oppositely phased currents through them.

The coils 15 shown in FIG. 3 may be advantageously arranged on a common carrier plate 25, which simplifies their mounting and mutual alignment. Advantageously, they are designed as concentric conducting leads on carrier 25, implemented as a multi-layer printed circuit.

In the embodiment shown in FIG. 3, carrier plate 25 lies against a wall section 26 of housing 1 that forms measuring surface 2. Advantageously, carrier plate 25 is laminated to wall section 26. Alternatively, carrier plate 25 can form the outer wall of housing 1 and therefore measuring surface 2 itself. Both these embodiments allow positioning of coils 15 close to and in very well defined spatial relation relative to the surface of brake disk 4. In particular, the distance between coils 15 and the sample does not vary when the force pressing the one against the other changes. This is important because a variation of the distance by only a few tenths of a millimeter can lead to very large signal variations.

Coils 15 have a diameter that corresponds approximately to the half thickness of the sample such that their field extends sufficiently deep into the brake disk 4 without a substantial part of the field exiting from the opposite side of brake disk 4. In order to fulfill these requirements for typical brake disks, an advantageous diameter of coils 15 is in a range between 10-15 mm. If the coils are non-rotationally symmetric, this is the diameter tangential to the brake disk if the measuring device is applied in its measuring position against brake disk 4.

Figure 5:
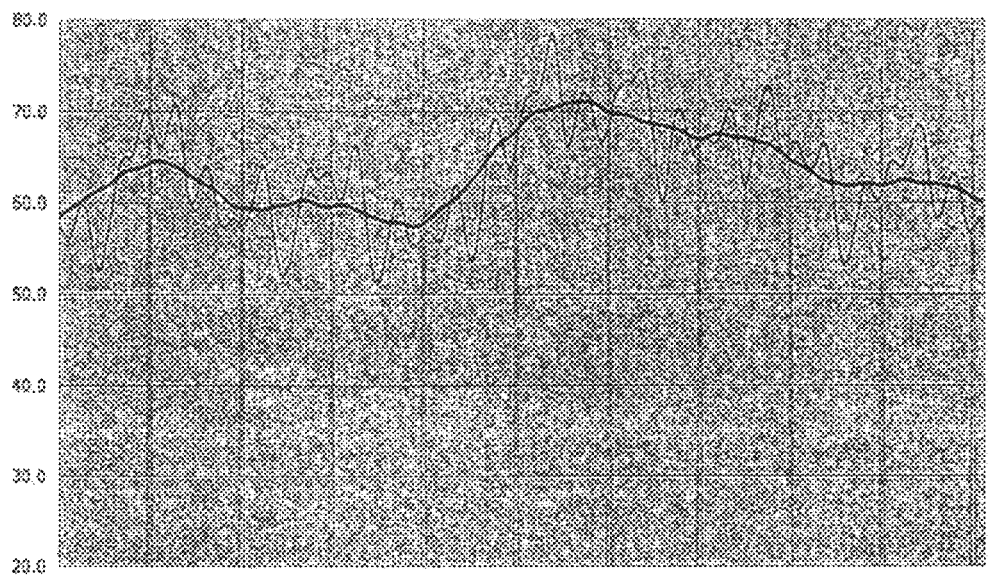
FIG. 5 shows a measured value as a function of the angle.

A review of FIG. 5 shows that the selected geometry satisfies the requirements. The wiggly line shows the position dependence of the signal when measuring with a single coil whose diameter corresponds approximately to the disk thickness. A part of the modulation is caused by the venting channels—overlaid and non-periodic are variations due to the natural inhomogeneity of the composite. The smoothed curve is created when sampling with the device described here. The vertical axis shows the measuring value, in linear units, the horizontal axis the angle or azimuthal position of the device along the outer edge of the brake disk 4.

Figure 6:
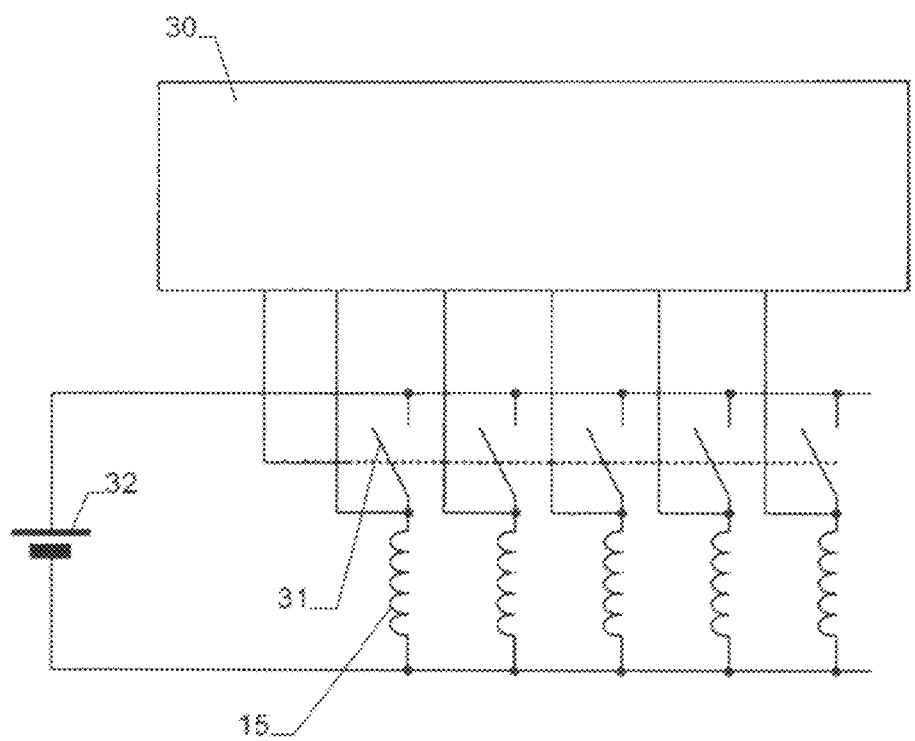
FIG. 6 is a partial block circuit diagram of the device.

FIG. 6 shows a possible embodiment of the coil circuit. Accordingly, a driver 30 is provided, which controls the operation of coils 15 and generates a magnetic field in measuring area 18 via coils 15. An electronic switch 31 is attributed to or associated with each coil, i.e., coils 15 can, by closing switches 31, be connected, parallel to each other and to the supply voltage from a voltage source 32. This parallel configuration allows using a voltage source 32 with low voltage and without voltage converter, such as a simple battery. When switches 31 are interrupted, coils 15 are disconnected from the voltage supply and an inductive voltage is generated over each coil due to the eddy currents in brake disk 4. These inductive voltages are added computatively or electrically by driver 30. In this manner, a comparatively strong signal is generated even if only a low supply voltage is used.

Advantageously, as shown in FIG. 1, the device has an interface 39 for exchanging data with external equipment, e.g., in order to generate a protocol of the measurements that have been carried out. Further, one or more buttons 40 can be arranged on the device for storing and/or marking a current measuring value.

In principle, it is also possible to equip the device with a single coil only, which has an arcuate cross section. However, as such a coil has a high inductance, it needs more power and is slower in operation. In addition, its field reaches deeply, which gives rise to a risk that components arranged behind the brake disk may be included in the measurement. For these reason, it is advantageous to use several coils, and in particular more than three coils.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A device for determining wear in a carbon ceramic brake disk, comprising:
   a coil arrangement having more than three coils structured and arranged to generate a magnetic field in an arcuate measuring area in the brake disk and to detect an eddy current in the brake disk, wherein each coil extends around a center and the centers of the coils are arranged on an arcuate curve;
   a housing;
   exactly two stops arranged on the housing being structured and arranged to radially abut against the brake disk; and
   a measuring surface structured and arranged to abut against a front side of the brake disk, wherein the stops comprise projections extending transversally to the measuring surface, wherein said stops are projections extending over said measuring surface.

2. The device of claim 1, wherein the arcuate measuring area is positionable in a ring having a radial width smaller than 2 cm and an inner radius between 10 and 15 cm, and a length tangentially along the ring of at least 8 cm.

3. The device of claim 1, further comprising a common carrier plate on which the coils are arranged.

4. The device of claim 3, wherein the coils are formed by conductive leads on the carrier plate.

5. The device of claim 1, wherein each coil extends around a center and the centers of the coils are arranged on an arcuate curve.

6. The device of claim 5, wherein the centers of the coils are arranged on a segment of a circle.

7. The device of claim 1, wherein each coil extends around a center and the centers of the coils are arranged on at least two arcuate, parallel curves.

8. The device of claim 7, wherein the centers of the coils are arranged on at least two segments of concentric circles.

9. The device of claim 8, further comprising a common carrier plate on which the coils are arranged, wherein the common carrier plate one of forms a measuring surface and abuts on an inner side of a wall section forming the measuring surface.

10. The device of claim 7, wherein each two neighboring coils on different curves are poled anti-parallel to each other.

11. The device of claim 1, further comprising a voltage supply and a driver, wherein the driver is structured and arranged to connect the coils, in parallel to each other, to the voltage supply.

12. The device of claim 11,
    wherein the driver is structured and arranged
       to disconnect the coils from the voltage supply and to sum inductive voltages generated over the coils after disconnecting the coils from the voltage supply.

13. The device of claim 1, wherein mutually neighboring coils are poled anti-parallel to each other.

14. The device of claim 1, wherein the projections comprise rollers.

15. The device of claim 1, further comprising
a light source for generating a light field as a positioning aid,
wherein the light source and the stops are mutually arranged to generate a light strip on a front face of the brake disk upon abutting the device against the brake disk.

16. The device of claim 1, further comprising a light source structured and arranged to generate a light field as a positioning aid.

17. The device of claim 1, wherein a diameter of the at least one each of the coils is between 10 and 15 mm.

* * * * *